US008682418B2

(12) United States Patent
Tanaka

(10) Patent No.: US 8,682,418 B2
(45) Date of Patent: Mar. 25, 2014

(54) DIAGNOSIS SUPPORTING APPARATUS AND CONTROL METHOD OF DIAGNOSIS SUPPORTING APPARATUS

(75) Inventor: Kenichi Tanaka, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/564,127

(22) Filed: Aug. 1, 2012

(65) Prior Publication Data

US 2012/0296220 A1    Nov. 22, 2012

Related U.S. Application Data

(63) Continuation of application No. PCT/JP2011/079798, filed on Dec. 22, 2011.

(30) Foreign Application Priority Data

Feb. 1, 2011  (JP) ................................ 2011-019986

(51) Int. Cl.
*A61B 6/00*      (2006.01)
(52) U.S. Cl.
USPC ......................................... 600/476; 600/109
(58) Field of Classification Search
USPC ................................................ 600/109, 476
See application file for complete search history.

(56) References Cited

U.S. PATENT DOCUMENTS

| 5,754,676 A | 5/1998 | Komiya et al. |
| 2006/0050966 A1 | 3/2006 | Nishimura et al. |
| 2008/0058593 A1* | 3/2008 | Gu et al. ...................... 600/109 |
| 2009/0074269 A1 | 3/2009 | Nishimura et al. |
| 2009/0074270 A1 | 3/2009 | Tanaka et al. |
| 2010/0069747 A1 | 3/2010 | Watanabe et al. |
| 2010/0309299 A1* | 12/2010 | Kubo et al. ..................... 348/68 |
| 2011/0082335 A1* | 4/2011 | Omori et al. .................. 600/109 |

FOREIGN PATENT DOCUMENTS

| EP | 1 568 307 A1 | 8/2005 |
| EP | 1 618 828 A1 | 1/2006 |
| EP | 1 870 020 A1 | 12/2007 |
| EP | 1 994 878 A1 | 11/2008 |
| EP | 1 994 880 A1 | 11/2008 |
| EP | 2 033 567 A1 | 3/2009 |
| EP | 2 163 191 A1 | 3/2010 |
| JP | 09-251535 | 9/1997 |
| JP | 2004-181096 | 7/2004 |

(Continued)

OTHER PUBLICATIONS

European Search Report dated Mar. 5, 2013 from corresponding European Patent Application No. 11 85 7725.3.

*Primary Examiner* — Unsu Jung
*Assistant Examiner* — Christopher Cook
(74) *Attorney, Agent, or Firm* — Scully, Scott, Murphy & Presser, P.C.

(57) ABSTRACT

A diagnosis supporting apparatus includes: an image input section that inputs an endoscopic image acquired from a living tissue, a structure detection section that detects similar circular-shaped structures from an image signal corresponding to the endoscopic image inputted to the image input section, and a network detection section that detects a predetermined network shape in the endoscopic image, based on a number of similar circular-shaped structures detected by the structure detection section, areas of the similar circular-shaped structures, distances between the respective similar circular-shaped structures, or a number of connections between the respective similar circular-shaped structures.

12 Claims, 7 Drawing Sheets

(56) References Cited

FOREIGN PATENT DOCUMENTS

| JP | 2006-141734 | | 6/2006 |
| JP | 2007-244519 | | 9/2007 |
| JP | 2008104886 | * | 11/2007 |
| JP | 2010-068865 | | 4/2010 |
| JP | 2010-179042 | | 8/2010 |
| WO | WO 2007/119297 | | 10/2007 |

* cited by examiner

DIAGNOSIS SUPPORTING APPARATUS AND CONTROL METHOD OF DIAGNOSIS SUPPORTING APPARATUS

CROSS REFERENCE TO RELATED APPLICATION

This application is a continuation application of PCT/JP 2011/079798 filed on Dec. 22, 2011 and claims benefit of Japanese Application No. 2011-019986 filed in Japan on Feb. 1, 2011, the entire contents of which are incorporated herein by this reference.

BACKGROUND OF THE INVENTION

1. Field of the Invention

The present invention relates to a diagnosis supporting apparatus which performs an image processing for supporting diagnosis on an endoscopic image of a living tissue, and a control method of the diagnosis supporting apparatus.

2. Description of the Related Art

In recent years, endoscopes have been widely used in medical fields, and such endoscopes are configured to be capable of picking up an image of a living mucosa and the like of an inner wall of a digestive tract by inserting an insertion portion into a body cavity such as the digestive tract, and displaying the picked-up image as an endoscopic image.

In addition, research has been carried out regarding an image processing for supporting diagnosis using running patterns of blood vessels under a living mucosa and an epithelium (or epithelial tissue) in an endoscopic image picked up with an endoscope.

On the other hand, the prior art example in Japanese Patent Application Laid-Open Publication No. 9-251535 discloses an image processing method used with respect to medical image data acquired by a breast X-ray photograph (mammogram), wherein a pixel at which the vector intensity of gray level gradient is maximal is searched for in each of a plurality of search directions which are radially spread from an arbitrary pixel to peripheral pixels, a feature value related to gray level gradient is calculated from the vector intensity of gray level gradient and an amount of angle difference between the vector direction and the search direction at each of the searched plurality of pixels, and based on the feature value, pattern detection for determining whether or not the arbitrary pixel is included in a predetermined pattern is performed. This prior example provides a detection method for detecting an image of microcalcification with high accuracy in order to support early detection of a breast cancer.

A living mucosa as a normal tissue in the stomach and the like has microvessels running so as to formulate a honeycomb-shaped network. On the other hand, a living mucosa of a lesion part such as a living mucosa of a neoplastic lesional tissue changes to have a structure or a shape which is deviated or different from the honeycomb-shaped network of a normal living mucosa.

SUMMARY OF THE INVENTION

A diagnosis supporting apparatus according to one aspect of the present invention includes: an image input section configured to input an endoscopic image acquired from a living tissue; a structure detection section configured to detect similar circular-shaped structures from an image signal corresponding to the endoscopic image inputted to the image input section; and a network detection section configured to detect a predetermined network shape in the endoscopic image, based on a number of the similar circular-shaped structures detected by the structure detection section, areas of the similar circular-shaped structures, distances between the respective similar circular-shaped structures, or a number of connections between the respective similar circular-shaped structures.

A control method of a diagnosis supporting apparatus according to one aspect of the present invention includes: an image input step in which an image input section inputs an endoscopic image acquired from a living tissue; a structure detection step in which a structure detection section detects similar circular-shaped structures from an image signal corresponding to the endoscopic image inputted in the image input step; and a network detection step in which a network detection section detects a predetermined network shape in the endoscopic image, based on a number of the similar circular-shaped structures detected in the structure detection step, areas of the similar circular-shaped structures, distances between the respective similar circular-shaped structures, or a number of connections between the respective similar circular-shaped structures.

DETAILED DESCRIPTION OF THE PREFERRED EMBODIMENT(S)

Figure 1:
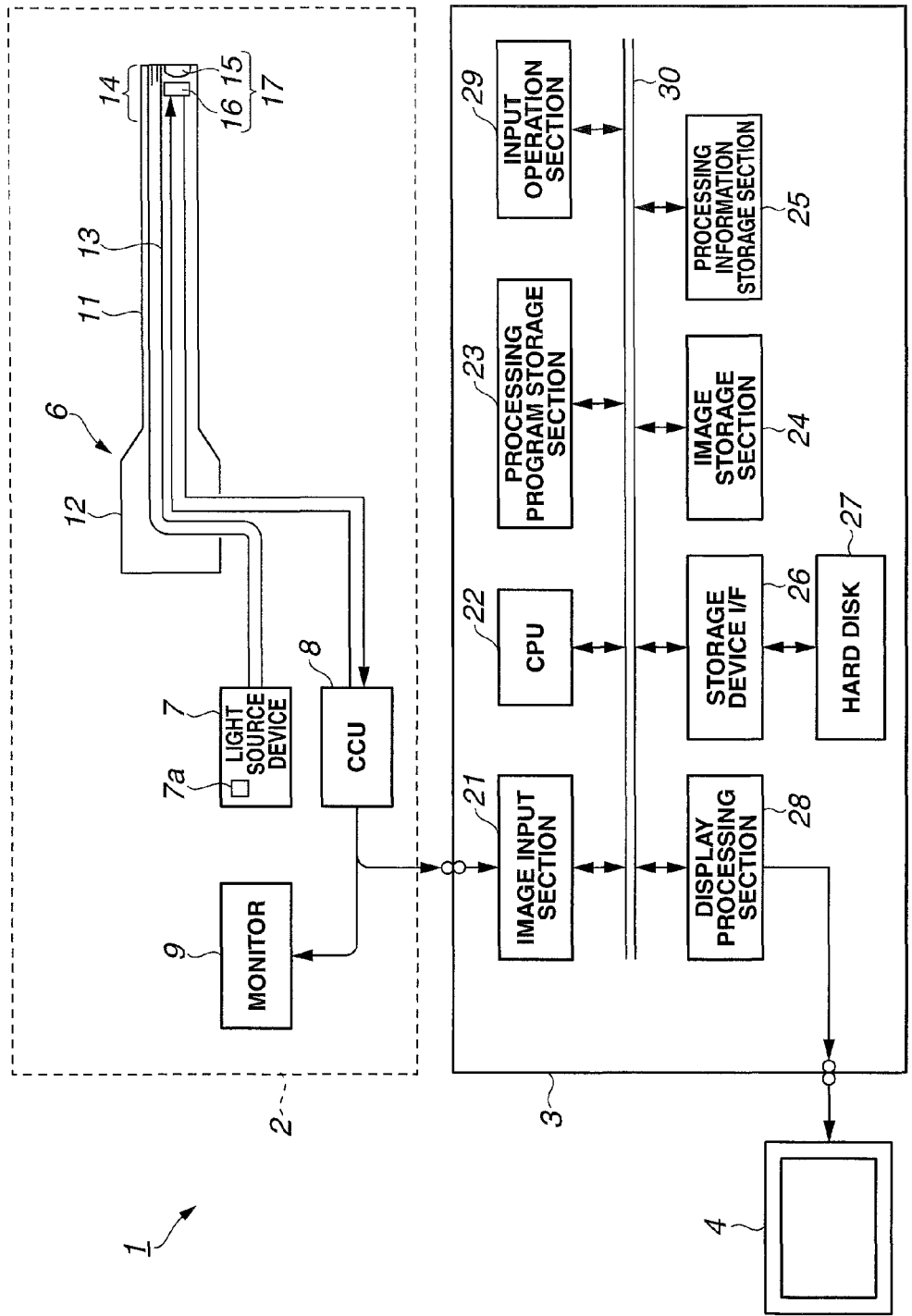
FIG. 1 is a configuration diagram showing an overall configuration of a diagnosis supporting apparatus according to a first embodiment of the present invention.

Hereinafter, embodiments of the present invention will be described with reference to drawings.

(First Embodiment)

A diagnosis supporting apparatus 1 according to the first embodiment of the present invention shown in FIG. 1 includes: an endoscope apparatus 2; a medical image processing apparatus (hereinafter, shortly referred to as image processing apparatus) 3 configured by a personal computer which performs an image processing on an endoscopic image acquired by the endoscope apparatus 2; and a monitor 4 which displays an image subjected to the image processing by the image processing apparatus 3.

The endoscope apparatus 2 includes: an endoscope 6 which is configured to be inserted into a body cavity and which forms an in-vivo image pickup apparatus which picks up an image inside a body; a light source device 7 which supplies illumination light to the endoscope 6; a camera control unit (abbreviated as CCU) 8 as a signal processing apparatus which performs a signal processing on image pickup means of the endoscope 6; and a monitor 9 which receives an image signal outputted from the CCU 8 and displays the image picked up by the image pickup device as an endoscopic image.

The endoscope 6 includes an insertion portion 11 configured to be inserted into a body cavity and an operation portion 12 provided at a rear end of the insertion portion 11. In the insertion portion 11, a light guide 13 for transmitting illumination light is inserted.

A rear end of the light guide 13 is connected to the light source device 7. The illumination light supplied from the light source device 7 is transmitted by the light guide 13, and (the transmitted illumination light is) emitted from a distal end surface attached to an illumination window provided at a distal end portion 14 of the insertion portion 11, to illuminate a living tissue as a target to be examined (diagnosis target) by the endoscope apparatus 6. Note that the light source device 7 supplies white illumination light for normal observation, or frame-sequential illumination light of red (R), green (G), and blue (B) which covers white color to the light guide 13. Therefore, a living tissue as the target to be examined is irradiated with white light.

In addition, the endoscope apparatus 2 is provided with a switch for switching an observation mode, not shown, through which the observation mode can be switched from the normal observation mode to a narrow-band observation mode. In this case, the light source device 7 switches a filter to a narrow-band filter configured to transmit narrow-band light, and supplies narrow-band illumination light to the light guide 13 to irradiate the living tissue as a target to be examined with the narrow-band light. To this end, the light source device 7 includes a narrow-band light generation section 7a (which generates narrow-band light) for emitting the narrow-band light.

An objective lens 15 is attached to the observation window adjacent to the illumination window, and a charge coupled device (abbreviated as CCD) 16, for example, as a solid-state image pickup device is disposed at an image-forming position of the objective lens 15. The objective lens 15 and the CCD 16 configure an image pickup section 17 which picks up an image with reflected light from a living tissue. An optical image formed on the image pickup surface of the CCD 16 is photoelectrically converted by the CCD 16.

The CCD 16 is connected to the CCU 8 via a signal line, and the CCD 16 receives a CCD drive signal from the CCU 8, thereby outputting a photoelectrically converted image signal. The image signal is subjected to a signal processing in an image processing circuit in the CCU 8, and converted into an image signal to be displayed on a display device. The image signal is outputted to the monitor 9, and an endoscopic image is displayed on a display screen of the monitor 9. The image signal is inputted also to the image processing apparatus 3.

In the present embodiment, the distal end portion 14 of the insertion portion 11 of the endoscope 6 is inserted from an oral part of a patient to pickup an image of living mucosa from the esophagus to the gastric fundus, and the CCU 8 generates an image signal of the endoscopic image of the living mucosa.

The image processing apparatus 3, which receives the image signal, performs an image processing as described later, thereby determining whether the living mucosa subjected to the image processing has a structure of normal living mucosa as a predetermined living mucosal structure or has a structure of lesional mucosa such as neoplastic living mucosa. The image processing apparatus 3 further notifies the surgeon of the determination result by displaying the determination result on the monitor 4, thereby capable of supporting the surgeon when the surgeon performs diagnosis. The monitor 4 thus forms a notification section for notifying the determination result.

The surgeon refers to the determination result displayed on the monitor 4, thereby capable of smoothly and efficiently performing diagnosis without missing a neoplastic living tissue and the like.

The image processing apparatus 3 includes: an image input section 21 as image input means which inputs an endoscopic image generated by the endoscope apparatus 2; a CPU 22 as a central processing unit which performs an image processing on the image signal (also referred to as image signal data) acquired by digitalizing the image signal corresponding to the endoscopic image inputted from the image input section 21; and a processing program storage section 23 which stores processing program (control program) for causing the CPU 22 to perform the image processing. Note that the image input section 21 may be provided on the endoscope apparatus 2 side.

In addition, the image processing apparatus 3 includes: an image storage section 24 which stores image signal data and the like inputted from the image input section 21; a processing information storage section 25 which stores (processed) image data processed by the CPU 22 and processing information; a hard disk 27 as a storage device which stores the image data processed by the CPU 22, processing information, and the like via a storage device interface 26; a display processing section 28 which performs a display processing for displaying the image data processed by the CPU 22 and the like; and an input operation section 29 composed of a keyboard and the like through which a user such as a surgeon performs input of data such as parameters for the image processing and instruction operation.

Then, the image signal generated by the display processing section 28 is outputted to the display monitor 4, and the processed image subjected to the image processing, and the like, are displayed on the display screen of the display monitor 4. Note that, the image input section 21, the CPU 22, the processing program storage section 23, the image storage section 24, the processing information storage section 25, the storage device interface 26, the display processing section 28, and the input operation section 29 are connected to one another via a data bus 30.

Figure 2:
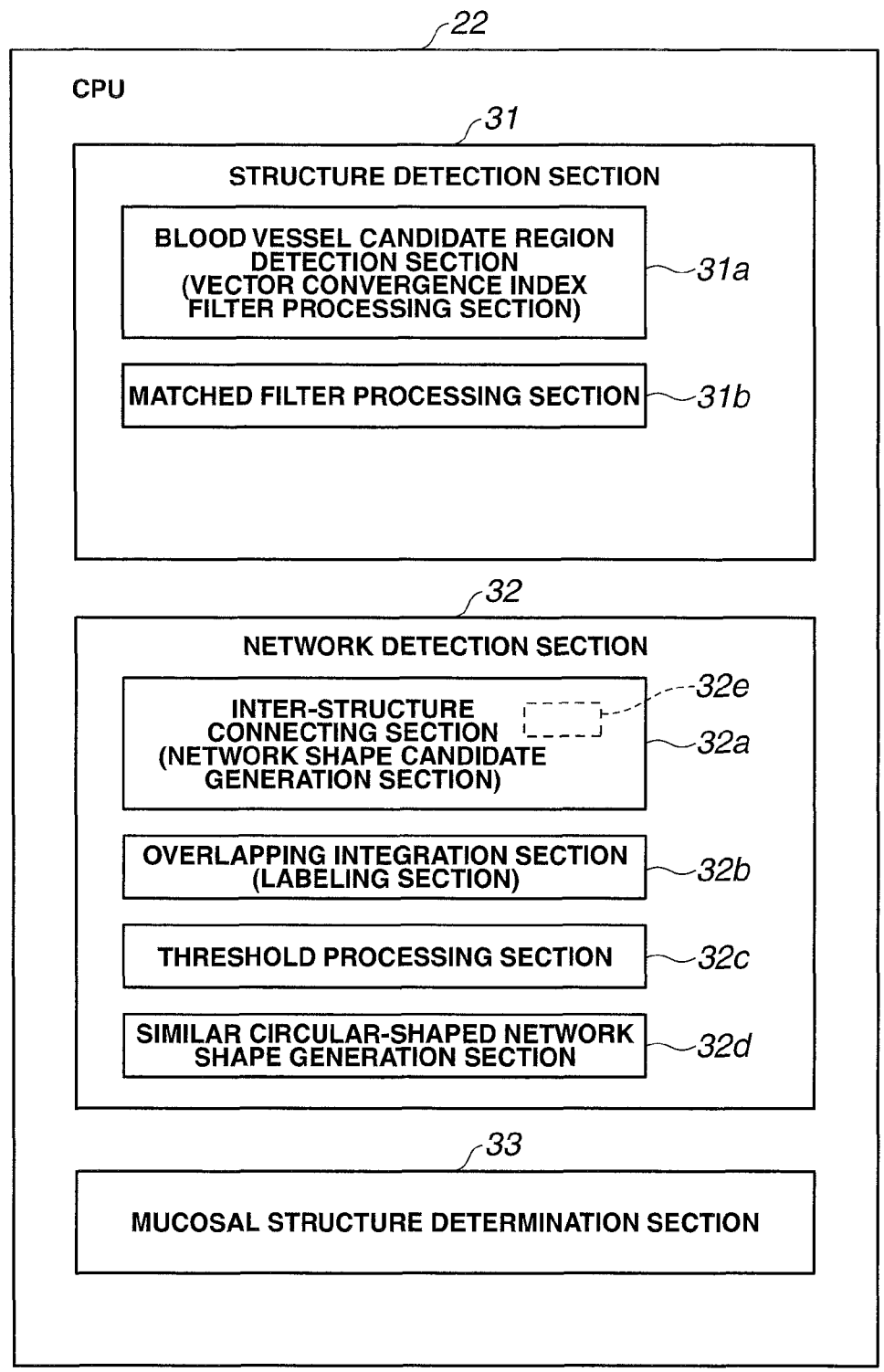
FIG. 2 is a block diagram illustrating processing blocks in a CPU configuring an image processing apparatus.

In the present embodiment, as shown in FIG. 2, for example, the CPU 22 includes processing functions of a structure detection section 31 as structure detection means which detects similar circular-shaped structures included in a normal living mucosa from image signal data, and a network detection section 32 as network detection means which detects a predetermined network shape, based on the number of the similar circular-shaped structures detected by the structure detection section 31, or areas of the similar circular-shaped structures, the distances between the respective similar circular-shaped structures, or the number of connections between the respective similar circular-shaped structures.

In addition, in the present embodiment, the CPU 22 further includes a processing function of a mucosal structure determination section 33 which determines whether or not the endoscopic image includes a predetermined mucosal structure as a diagnosis target, based on a determination result indicating whether or not the region having the predetermined network shape detected by the network detection section 32 is equal to or larger than a threshold in a region (target region) of the endoscopic image in which the region having the predetermined network shape is detected.

Note that, without using the CPU 22, the structure detection section 31, the network detection section 32, and mucosal structure determination section 33 may be respectively formed by hardware. In addition, in FIG. 2, the network detection section 32 may be configured to include the mucosal structure determination section 33, for example.

In the present description, the term "similar circular-shape" means a shape similar to a circle. Accordingly, the similar circular shape includes an elliptical shape, and polygonal shape such as honeycomb-shaped hexagon, for example, which can approximate a circle shape, not to mention a circular shape such as a true circle.

The structure detection section 31 includes: a blood vessel candidate region detection section 31a which detects a blood vessel candidate region as a region of blood vessel candidate from the endoscopic image by using a vector convergence index filter with respect to the image signal data; and a matched filter processing section 31b which performs a matched filter processing in which a similar circular-shaped filter is applied to the detected blood vessel candidate region in order to detect similar circular-shaped structures, thereby extracting a part (or small region) having a high correlation with (the similar circular shape of) the similar circular-shaped filter.

Furthermore, the network detection section 32 includes an inter-structure connecting section 32a, and regarding (the part or small region of) the respective similar circular-shaped structures detected by the structure detection section 31, when distances between each of the similar circular-shaped structures and other similar circular-shaped structures therearound are equal to or smaller than a predetermined distance, the inter-structure connecting section 32a respectively connects (joints) the similar circular-shaped structures to each other by adding regions having predetermined areas set respectively according to the distances.

Then, the network detection section 32 determines an overlapping degree of the regions in an aggregation of the regions having predetermined areas which have been generated by the inter-structure connecting section 32a with respect to all of the similar circular-shaped structures detected by the structure detection section 31, and detects a candidate region having a predetermined network shape based on the aggregation of the regions having an overlapping degree which is equal to or larger than a first threshold.

That is, the network detection section 32 includes the inter-structure connecting section 32a which is configured to perform a processing with respect to the respective image signals including the similar circular-shaped structures detected (extracted) by the matched filter processing section 31b such that, when distances between each of the similar circular-shaped structures and other similar circular-shaped structures therearound are equal to or smaller than the predetermined distance, the inter-structure connecting section 32a connects (joints) between the similar circular-shaped structures by respectively adding regions having predetermined areas corresponding to the respective distances between the similar circular-shaped structures (generates a similar circular-shaped network shape candidate).

Thus, when generating the similar circular-shaped network shape candidate (or similar circular-shaped network shape candidate region) by connecting (jointing) between the respective similar circular-shaped structures, the inter-structure connecting section 32a connects the similar circular-shaped structures which satisfy the condition that the distances between the respective similar circular-shaped structures are equal to or smaller than a threshold in a case where a predetermined distance is set as the threshold.

In other words, the inter-structure connecting section 32a shown in FIG. 2 includes a determination section 32e, as shown with dotted lines, which determines whether or not the distances between the respective similar circular-shaped structures are equal to or smaller than the threshold. Only with respect to the similar circular-shaped structures which satisfy the condition that the distances between the respective similar circular-shaped structures are equal to or smaller than the threshold, which have been determined by the determination section 32e, the inter-structure connecting section sets regions having the (predetermined) areas corresponding to the respective distances between the similar circular-shaped structures and generates a similar circular-shaped network shape candidate (or similar circular-shaped network shape candidate region) by connecting (jointing) between the similar circular-shaped structures peripheral to each other. In the specific example in FIG. 8 to be described later, the similar circular-shaped structures are connected to each other by respectively setting regions having areas of squares whose diagonal lines correspond to the distances between the similar circular-shaped structures which satisfy the condition of distance.

In addition, the inter-structure connecting section 32a connects (joints) between a plurality of similar circular-shaped structures by respectively adding the regions having predetermined areas corresponding to the above-described distances to generate an aggregation of the regions having the predetermined areas which becomes a similar circular-shaped network shape candidate. The inter-structure connecting section 32a can be thus regarded as a network shape candidate generation section which generates a network shape candidate.

Furthermore, the network detection section 32 includes an overlapping integration section (labeling section) 32b which integrates, with respect to the similar circular-shaped network shape candidate generated by the inter-structure connecting section 32a, each of the aggregation of the regions which have predetermined areas and at least parts of which are overlapped with each other, as a block, and attaches a label to the block.

In addition, the network detection section 32 includes a threshold processing section 32c which performs a threshold processing for deleting a block having the number of overlapping which is equal to or smaller than a threshold with respect to the blocks formed by integration and respectively attached with labels, and a similar circular-shaped network shape generation section 32d which generates a similar circular-shaped network shape (as a predetermined network shape) by performing, with respect to the labeled block which remains after the threshold processing, a processing for forming the outside of the block in a convex shape outwardly.

The mucosal structure determination section 33 determines whether the endoscopic image includes a predetermined mucosal structure depending on whether or not a region having the generated similar circular-shaped network shape exists in the endoscopic image of a processing target at a rate equal to or larger than a threshold, and notifies the determination result, thereby supporting the surgeon.

Thus, the diagnosis supporting apparatus 1 according to the present embodiment includes: the image input section 21 as the image input means which inputs an endoscopic image acquired from a living tissue; the structure detection section 31 as the structure detection means which detects the similar circular-shaped structures from the image signal corresponding to the endoscopic image inputted to the image input means; and the network detection section 32 as the network detection means which detects the predetermined network shape, based on the number of similar circular-shaped structures detected by the structure detection means, the areas of the similar circular-shaped structures, the distances between the respective similar circular-shaped structures, or the number of connections between the respective similar circular-shaped structures.

Next, the working of the present embodiment will be described with reference to the processing procedure in FIG. 3.

The endoscope 6 in the endoscope apparatus 2 which configures the diagnosis supporting apparatus 1 in FIG. 1 is inserted into the upper digestive tract, for example, by the surgeon. Specifically, the insertion portion 11 of the endoscope 6 is inserted from the oral part into inside of the stomach through the esophagus, to pick up an image of a living mucosa of the gastric fundic gland as a diagnosis target by the image pickup section 17 provided at the distal end portion. The CCU 8 performs a signal processing with respect to the image pickup section 17, generates an image signal of an endoscopic image, and displays the endoscopic image on the monitor 9.

Figure 4:
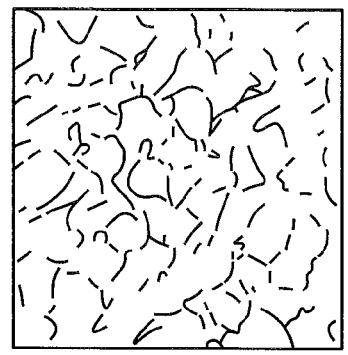
FIG. 4 is a pattern diagram illustrating an endoscopic image of a living mucosa of a normal gastric fundic gland.

FIG. 4 schematically shows the endoscopic image of the living mucosa of the normal gastric fundic gland, for example. In the living mucosa of the normal gastric fundic gland, microvessels run so as to construct a similar circular-shaped network shape which is similar to a honeycomb shape.

In this case, the living mucosa may be irradiated with the narrow-band light in the blue wavelength band which is generated by the narrow-band light generating section 7a, and the endoscopic image may be generated from the image pickup signal acquired by the image pickup section 17 by image pickup with the reflected light from the living mucosa. If such a narrow-band light in the blue wavelength band is used, an endoscopic image which more clearly reflects the mucosal structure near the surface layer of the living mucosa can be acquired compared with the case where the white light or broad-band light is used.

Figure 3:
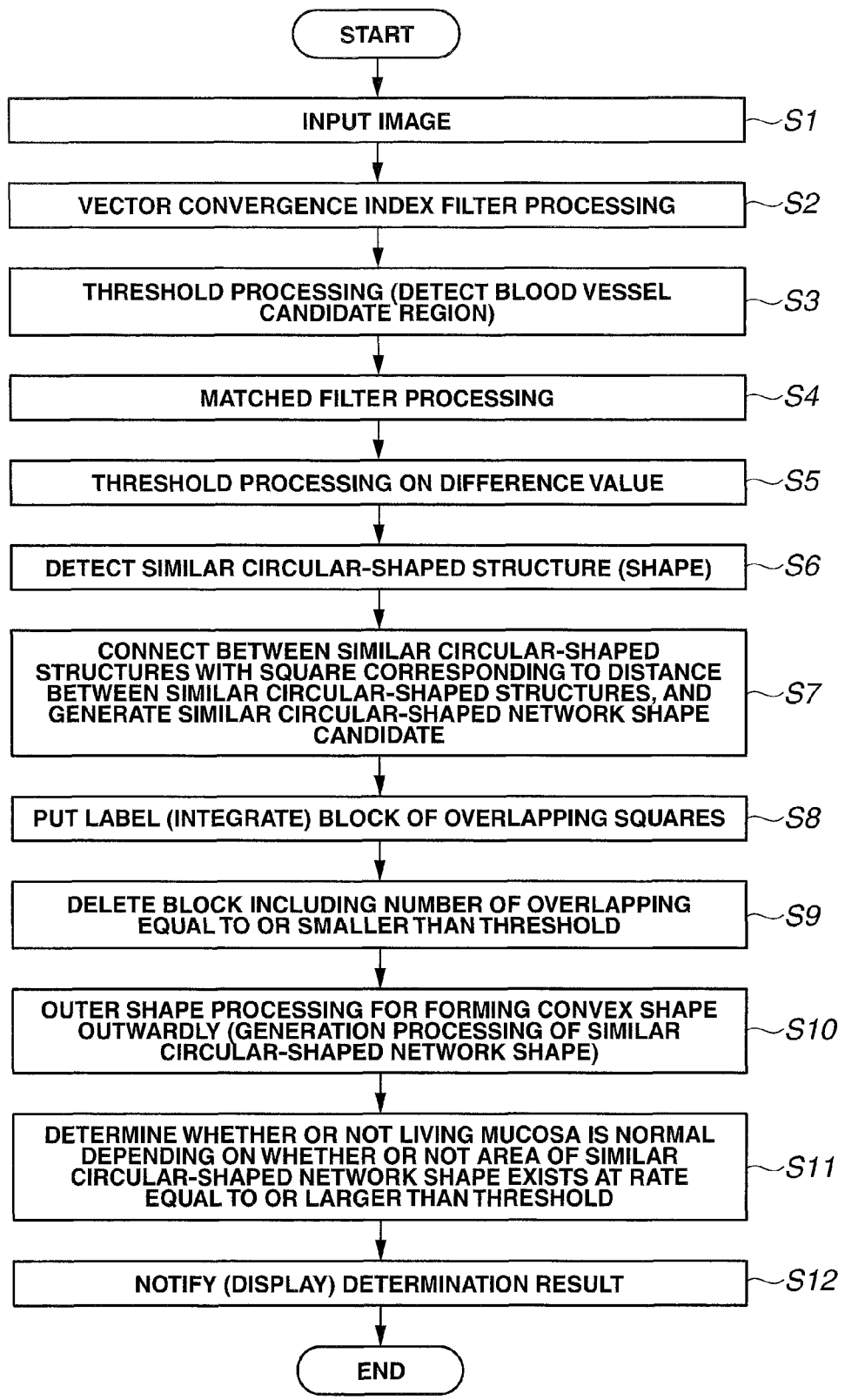
FIG. 3 is a flowchart describing a processing procedure according to the first embodiment.

As shown in the step S1 in FIG. 3, the endoscopic image is converted into digital image signal data by the image input section 21 and inputted to the CPU 22 in the image processing apparatus 3.

As shown in the step S2, the blood vessel candidate region detection section 31a of the CPU 22 performs a processing for detecting a blood vessel candidate region by a vector convergence index filter processing in which the vector convergence index filter is used with respect to the image signal data corresponding to the endoscopic image. Accordingly, in the present embodiment, the blood vessel candidate region detection section 31a is configured by a vector convergence index filter processing section using a vector convergence index filter. Note that the vector convergence index is used for evaluating to what extent the gradient vector in a region in the vicinity of a certain point of interest converges with respect to the certain point of interest, by focusing attention on the direction of the gradient vector of the change in the gray level in the image (signal data).

Note that, after a binary image is generated by performing a threshold processing on the image signal data, a blood vessel candidate region may be detected by the vector convergence index filter processing using the vector convergence index filter.

The vector convergence index filter processing is disclosed in FIG. 4 in Japanese Patent Application Laid-Open Publication No. 2008-104886, for example. In the present embodiment, the vector convergence index filter processing is performed on two-dimensional image signal data.

As shown in the next step S3, the blood vessel candidate region detection section 31a of the CPU 22 performs the threshold processing on the image signal data subjected to the vector convergence index filter processing. For example, binarization is performed on the image signal data after the vector convergence index filter processing such that pixels whose values are smaller than a threshold Thre 1 (Thre 1=0.6, for example) are set as pixel value being equal to zero, and pixels whose values are equal to or larger than the threshold Thre 1 are set as pixel value being equal to one, to detect (extract) the blood vessel candidate region.

Figure 5:
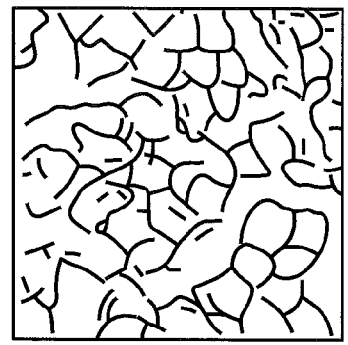
FIG. 5 illustrates an endoscopic image of a blood vessel candidate region detected by applying a vector convergence index filter.

FIG. 5 illustrates the pixels configuring the endoscopic image of the blood vessel candidate region extracted by the binarization. In this case, it is possible to make it easier to visually recognize the mucosal structure by coloring the blood vessel candidate region with a color different from the display color in FIG. 4. FIG. 5 shows a feature in which the running pattern of blood vessels in FIG. 4 is more sharpened (evident). Note that the figure may be allowed to be acquired as an endoscopic image in which the mucosal structure is enhanced by coloring the living mucosa as a diagnosis target by pigment dispersion or dyeing.

Figure 6:
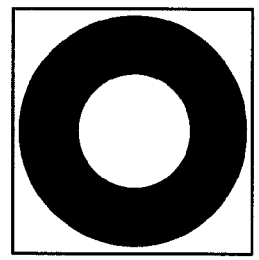
FIG. 6 illustrates an example of a matched filter.

In the next step S4, the matched filter processing section 31b of the CPU 22 performs a matched filter processing by applying an annular-shaped matched filter (as one specific example of the similar circular shape) shown in FIG. 6 to all the pixels in the image signal data of the endoscopic image in FIG. 5.

In the present embodiment, the matched filters shown in FIG. 6 include two kinds of filter sizes, one is 41×41 and the other is 51×51. The matched filters are applied to all the pixels in the image signal data in FIG. 5, with the white region set to −1, and with the black annular region set to 1. Note that the image signal data of the endoscopic image in FIG. 5 has a pixel size from about 200×200 to 250×250, for example.

Note that, in a case where the matched filters are applied, since the white region and the black region have different areas, an average of pixel values multiplied by the coefficient 1 and an average of pixel values multiplied by the coefficient −1 are calculated, to obtain a difference value of the both averages, thereby reducing the influence caused by the difference in the areas of the white region and the black region.

In addition, the matched filters are not limited to those shown in FIG. 6, and the shape, the size, the coefficient, the number of filters to be used may be changed.

In the next step S5, the CPU 22 performs a threshold processing on difference values (calculated in the previous step S4). Specifically, binarization is performed on the respective difference values such that pixels whose values are smaller than a threshold Thre 2 (Thre 2=0.2, for example) are set as the pixel value being equal to zero, and pixels whose values are equal to or larger than the threshold Thre 2 are set as the pixel value being equal to one.

Note that the matched filters of two kinds of sizes, that is, 41×41 and 51×51, are used in the present embodiment, and when the pixel value obtained as a result of processing performed by applying one of the matched filters is equal to or larger than the threshold Thre 2, the pixel value is set to one.

Figure 7:
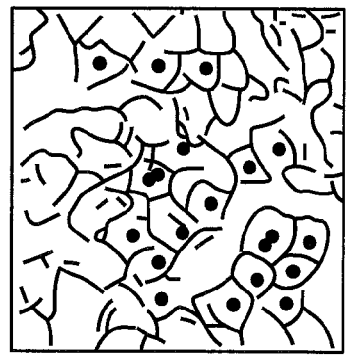
FIG. 7 illustrates that a processing result acquired in a case where a matched filter is applied to the endoscopic image of the blood vessel candidate region to detect similar circular-shaped structures is displayed on the endoscopic image.

FIG. 7 shows the endoscopic image acquired as a result of application of the matched filter, which was extracted by binarization. In FIG. 7, the pixel near the center in each of the similar circular-shaped regions detected as similar circular-shaped structures (shapes) has a pixel value of 1, and the pixel is shown with a black circle.

The binarization is thus performed by the threshold processing, and the part having the similar circular-shaped structures (portion having a high correlation with an annular shape) is detected (extracted) by performing the above-described image processing with respect to the endoscopic image of the living tissue of the diagnosis target as shown in step S6. Then, in the step S6, it is possible to perform labeling for discriminating the part having the similar circular-shaped structures where the pixel values are equal to 1 from the part (having a low correlation with the similar circular shapes) where the pixel values are equal to 0.

In the present embodiment, in the endoscopic image of the living tissue of the diagnosis target, a predetermined network shape as a feature value or an indicator which is closely related to the running pattern of the similar circular-shaped structures included in the endoscopic image is detected based on at least one of the number of similar circular-shaped structures detected as described below, the areas thereof, the distances between the respective structures, and the number of connections between the structures.

Therefore, in the step S7 in FIG. 3, the inter-structure connecting section 32a which configures the network detection section 32 of the CPU 22 connects between the respective similar circular-shaped structures by respectively adding (regions having) areas corresponding to the respective distances between the similar circular-shaped structures. In the case where the respective similar circular-shaped structures are connected to each other, only when the distances between the center points of the respective similar circular shaped structures are equal to or smaller than a threshold Thre 3 (Thre 3=40, for example), the structures are connected to each other by respectively adding predetermined areas (specifically, areas of squares) having diagonal lines which correspond to the distances between the structures (points). Note that, in the equation of Thre 3=40, one pixel is set as a unit distance 1, for example.

The aggregation of the structures connected by the predetermined areas (specifically, squares) forms a similar circular-shaped network shape candidate (candidate region). Accordingly, as described above, the inter-structure connecting section 32a forms a similar circular-shaped network shape candidate generation section which generates a similar circular-shaped network shape candidate.

Figure 8:
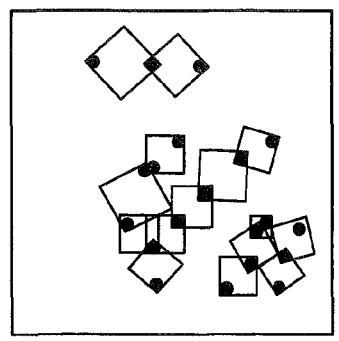
FIG. 8 illustrates a processed image in which the similar circular-shaped structures are respectively connected to each other with squares having areas corresponding to the respective distances between the similar circular-shaped structures.

FIG. 8 shows a processed image of the aggregations of the regions having areas of the squares which are similar circular-shaped network shape candidates obtained by performing the processing in the step S7 on the endoscopic image in FIG. 7. Note that the outline of the endoscopic image shown in FIG. 7 is omitted in FIG. 8. However, the processed image shown in FIG. 8 may be displayed in a superimposed manner on the endoscopic image.

In the present embodiment, the following processing is further performed to detect (calculate) the predetermined network shape region, and determination is made as to whether or not a predetermined mucosal structure is included by further performing the threshold processing using a threshold.

Figure 9:
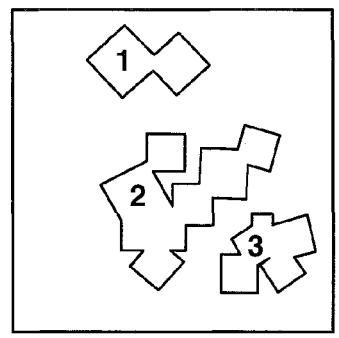
FIG. 9 illustrates that a label is attached to each block of the squares overlapped one another in the processed image in FIG. 8.

In the next step S8, the overlapping integration section (or labeling section) 32b of the CPU 22 puts a label on each of the blocks of the aggregations of the regions having areas of squares overlapped with each other, with respect to the image signal data of the processed image in FIG. 8, to integrate each of the aggregations as one block with a label. FIG. 9 shows a result of the integration. In FIG. 9, the aggregations are integrated as the blocks with the labels 1-3.

In the next step S9, the threshold processing section 32c of the CPU 22 removes, among the labeled blocks integrated and discretely scattered in the processed image in FIG. 9, the block in which the number of squares configuring the block (corresponding to the number of connections) is equal to or smaller than a threshold Thre 4 (Thre 4=5, for example). That is, a threshold processing using the threshold Thre 4 (or determination processing using the threshold) is performed on the processed image in FIG. 9, and the labeled block including the squares whose number is equal to or smaller than the threshold is deleted. In other words, only the block (aggregation) in which the number of connections between the similar circular-shaped structures is large is used for detecting the network shape.

Figure 10:
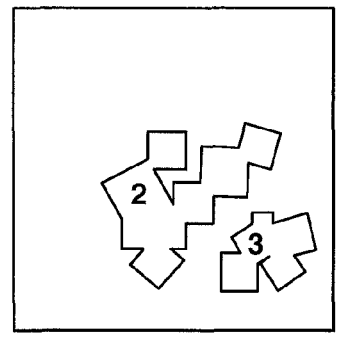
FIG. 10 illustrates a processing result acquired by performing a threshold processing on the processed image in FIG. 9 to remove a block which is equal to or smaller than a threshold.

FIG. 10 shows the image subjected to the processing in the step S9. Only the block with the label 1 is deleted, and the blocks with the labels 2, 3 are left.

In the present embodiment, the threshold processing in the step S9 has a function of the mucosal structure determination section 33 which performs a rough determination as to whether or not the endoscopic image as an object to be processed includes a predetermined mucosal structure. That is, when the living mucosa is normal, the processed image of the blocks determined to be equal to or larger than the threshold is left, as shown in FIG. 10.

In contrast, when the mucosa is a lesional mucosa greatly different from the living mucosa which is normal as the gastric fundic gland mucosa, if the same processing as described above is performed, the blocks in which the overlapping degree (that is, the number of connections) of the squares is small and which are aggregations of the small number of squares are left as shown in FIG. 12(E) by the processing in the step S8. Thus, only the blocks in which the overlapping degree is small are left, and as a result, only the blocks including the number of the squares which is smaller than the threshold Thre 4 are left when the threshold processing in step S9 is performed. Accordingly, if the mucosa is a lesional mucosa greatly different from the normal living mucosa, all the labeled blocks disappear by the threshold processing in the step S9.

That is, as described above, the threshold processing in the step S9 has the function of the mucosal structure determination section 33 which performs rough determination as to whether or not the predetermined mucosal structure is included.

Figure 11:
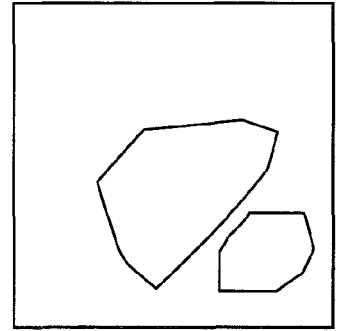
FIG. 11 illustrates a processed image acquired by performing a processing for forming an outer shape of the processed image in FIG. 10 in a convex shape.

In the next step S10, the similar circular-shaped network shape generation section 32d of the CPU 22 performs a processing for connecting the points at the part forming the outer shape of the block in the step S9 and forming the outer shape of the block in a convex shape outwardly. By performing this processing, a final similar circular-shaped network shape region as the predetermined network shape is generated. FIG. 11 shows the final similar circular-shaped network shape region generated by the processing in the step S10.

In the next step S11, the mucosal structure determination section 33 of the CPU 22 calculates a percentage of the area of the similar circular-shaped network shape region calculated in the step S10 in the endoscopic image, and determines whether or not the percentage is equal to or larger than a threshold Thre 5 (Thre 5=10 percent).

When the percentage of the calculated similar circular-shaped network shape region is equal to or larger than the threshold Thre 5 with respect to the area of the endoscopic image inputted to the image processing apparatus 3, the mucosal structure determination section 33 of the CPU 22 determines that the living mucosa corresponding to the endoscopic image is normal mucosal structure (in this case, normal gastric fundic gland mucosa).

On the other hand, the percentage is smaller than the threshold Thre 5, the mucosal structure determination section determines that the living mucosa corresponding to the endoscopic image is not a normal living mucosal structure (in this case, normal gastric fundic gland mucosa).

In the next step S12, the CPU 22 outputs to the monitor 4 the determination result in the step S11 and the percentage of the area of the similar circular-shaped network shape region as an evaluation value of the determination result, to notify (display) the surgeon of the determination result and the evaluation value of the determination result. The surgeon refers to the determination result indicating that the living mucosa is a normal gastric fundic gland mucosa and the evaluation value of the determination result, to perform diagnosis. Then, the processing steps in FIG. 3 are terminated.

In the above description, the processed image and the like are shown taking the case of the normal living mucosa as an example. However, if a similar processing is performed on the living mucosa of the lesion part, the image shown in FIG. 12 is acquired.

FIG. 12(A) illustrates the endoscopic image inputted to the image processing apparatus 3 in the step S1 in FIG. 3, and FIG. 12(B) illustrates the endoscopic image of the blood vessel candidate region extracted by binarization through the processings in the steps S2, S3.

FIG. 12(C) illustrates the processed image acquired as a result of applying the matched filter, which was extracted by performing binarization on the processed image shown in FIG. 12(B) or the endoscopic image shown in FIG. 12(A) through the processings in the steps S4, S5.

Figure 12:
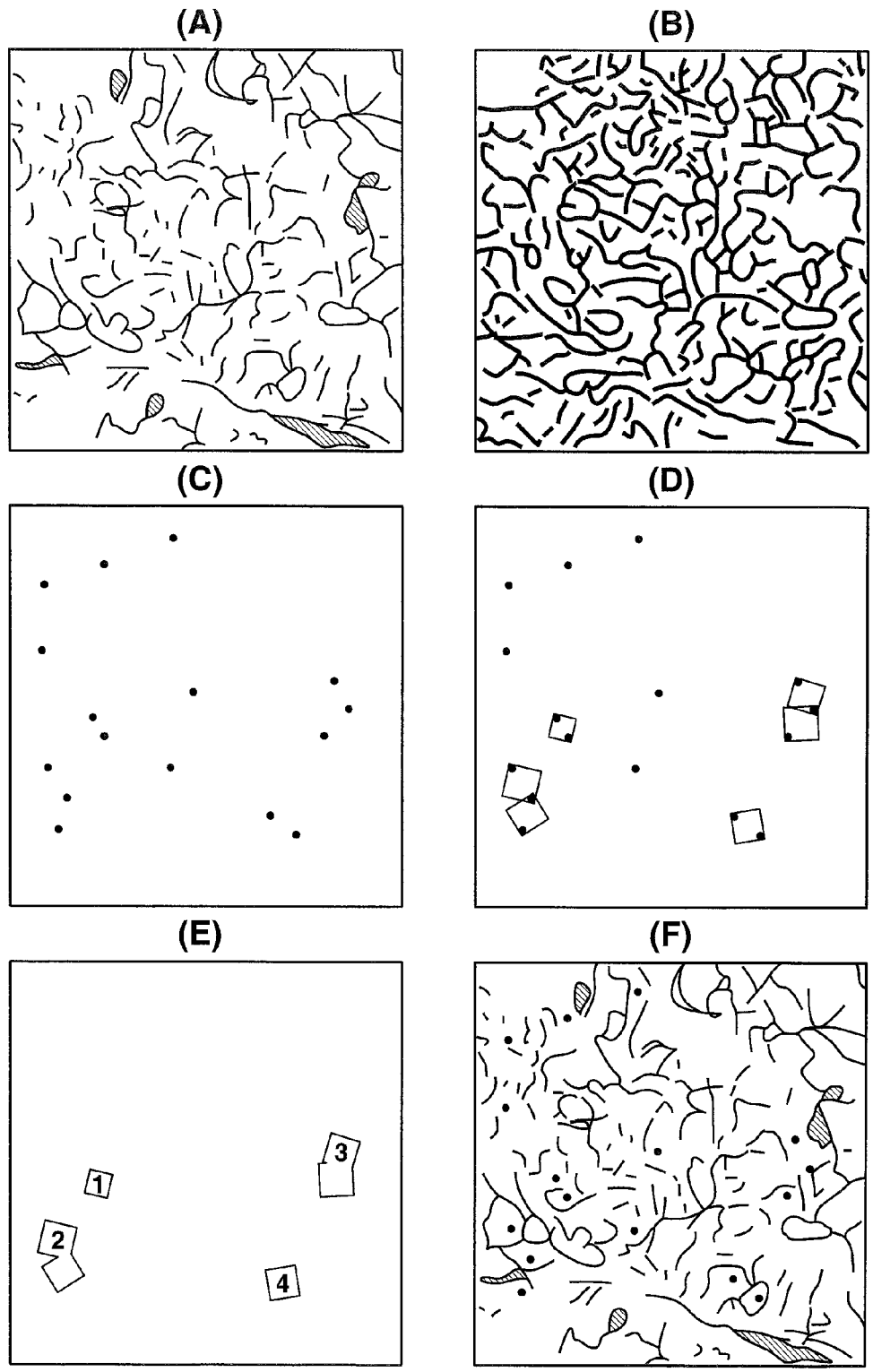
FIG. 12 illustrates a processing result acquired in a case where a processing similar to a processing performed on a living mucosa of a normal part is performed on a living mucosa of a lesion part.

Note that, the endoscopic image part in FIG. 12(B) or FIG. 12(A) are not shown in FIG. 12(C), but the pixel values larger than the threshold Thre 2, which are acquired by the threshold processing, are shown with the black circles. FIG. 12 (D) illustrates a processed image acquired by performing the processing in the step S7 on the processed image in FIG. 12(C), and in addition, FIG. 12(E) illustrates a processed image acquired by performing the processing in the step S8 on the processed image in FIG. 12(D).

The processed image in FIG. 12(E) shows a processed image of blocks with the labels 1 to 4, and the number of overlapping squares is smaller than that in the case of the normal mucosa shown in FIG. 9. Accordingly, if the processing in the step S9 is performed, the processed image of the blocks with the labels 1 to 4 is deleted, and as a result, the number of images becomes zero. FIG. 12(F) illustrates the result obtained by performing the processing in the step S9 on the image shown in FIG. 12(E). Note that, if FIG. 12(F) is displayed in the same display manner as in FIG. 12(E), the figure becomes blank. Therefore, FIG. 12(F) displays the processing result of FIG. 12(C) on the endoscopic image of FIG. 12(A) in a superimposed manner, for example.

In this case, the object to be processed does not exist in the step S10, and the living mucosa corresponding to the endoscopic image is determined not to be a normal mucosal structure (in this case, normal gastric fundic gland mucosa) in the step S11.

In the next step S12, the CPU 22 outputs the determination result in the step S11 and a percentage of the area of the similar circular-shaped network shape region as the evaluation value of the determination result to the monitor 4, to notify (display) the surgeon of the determination result and the evaluation value of the determination result.

The surgeon refers to the determination result indicating that the mucosal structure is not a normal gastric fundic gland mucosa and the evaluation value of the determination result to perform diagnosis. The surgeon can efficiently perform diagnosis on the lesion part and the like by referring to the determination result.

Thus, in the present embodiment, the similar circular-shaped structures included in the running pattern of the blood vessels in the case where the living mucosa is a normal mucosal structure are detected from the endoscopic image acquired by picking up the image of the living mucosa as the diagnosis target, and it is detected whether or not the predetermined network shape is included based on the number of detected similar circular-shaped structures, the areas thereof, and the like.

Furthermore, in the present embodiment, depending on whether or not the detected predetermined network shape, that is, the region of the similar circular-shaped network shape exists at a rate equal to or larger than the threshold with respect to the region of the endoscopic image in which the similar circular-shaped network shape is detected, determination is made as to whether or not the mucosal structure is normal, and the determination result is notified to the surgeon. As a result, as described above, the surgeon can efficiently perform diagnosis on the lesion part and the like by referring to the determination result.

Therefore, according to the present embodiment, it is possible to provide a diagnosis supporting apparatus which is capable of supporting the surgeon to perform diagnosis by detecting the predetermined network shape based on the number of similar circular-shaped structures, the areas thereof, and the like.

Note that, in the above-described first embodiment, description was made by taking the case of the living mucosa of the gastric fundic gland as an example. However, the present invention can be similarly applied also to an endoscopic image acquired by picking up images of I-type pit pattern (similar circular-shaped normal pattern) and II-type pit pattern (asteroid or papillary shape which is slightly larger pattern than the I-type normal pattern) of the colon, for example.

In addition, in the above-described first embodiment, instead of the matched filter processing section 31b, which uses a matched filter, in the structure detection section 31, a Hough transformation processing section which performs a Hough transformation processing may be used to detect the similar circular-shaped structures by the Hough transformation processing.

(Second Embodiment)

Next, the second embodiment of the present invention will be described. In the first embodiment, attention is focused on the running pattern of the blood vessels, and the similar circular-shaped structures are detected in order to detect the structure of the running pattern of the blood vessels. However, in the present embodiment, in order to detect the structure of the running pattern of the epithelial tissue, similar circular-shaped structures are detected. Then, based on the detection result, the diagnosis of the epithelial structure is supported.

Figure 13:
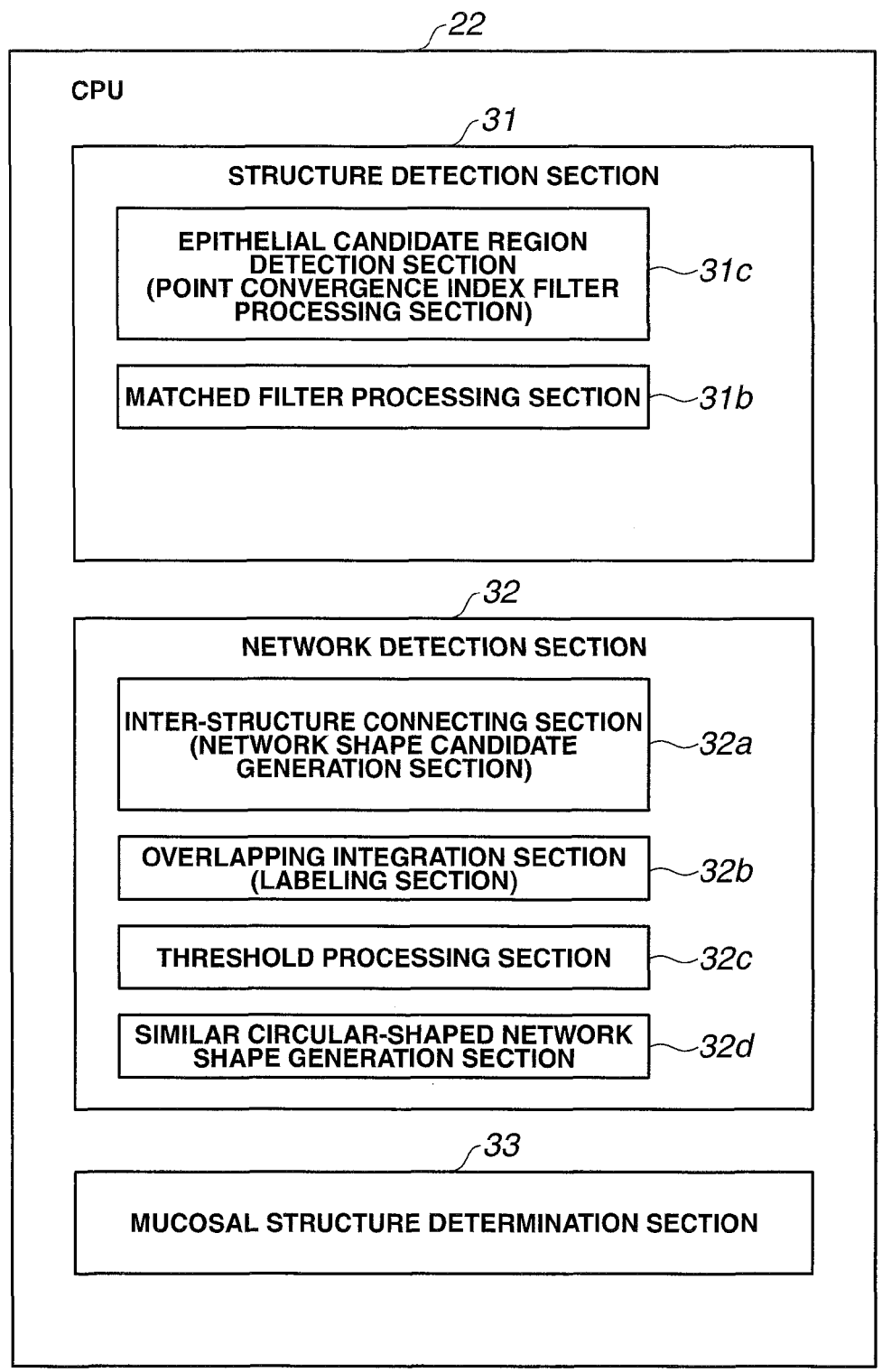
FIG. 13 is a block diagram illustrating processing blocks in a CPU according to a second embodiment of the present invention.

The present embodiment has almost the same hardware configuration as in the first embodiment shown in FIG. 1, but in the present embodiment, the processing functions of the structure detection section 31 performed by the CPU 22 are a little different from those in FIG. 2 according to the first embodiment. FIG. 13 is a block diagram of the processing functions performed by the CPU 22 according to the present embodiment.

A shown in FIG. 13, the CPU 22 includes the structure detection section 31, the network detection section 32, and the mucosal structure determination section 33. However, the CPU 22 is configured by using an epithelial candidate region detection section 31c instead of the blood vessel candidate region detection section 31a using the vector convergence index filter in FIG. 2.

In the present embodiment, the epithelial candidate region detection section 31c is configured by a point convergence index filter processing section which detects an epithelial candidate region using an iris filter as a point convergence index filter. Other configurations are the same as those in the first embodiment.

Therefore, since the processing in the present embodiment is similar to the processing shown in FIG. 3, only the points different from the processing in FIG. 3 are described.

In the present embodiment, a processing for detecting an epithelial candidate region is performed by using the iris filter as the point convergence index filter, instead of the vector convergence index filter in the step S2 in FIG. 3. In addition, the epithelial candidate region is detected instead of the blood vessel candidate region, by the threshold processing in the step S3 in FIG. 3.

In addition, in the present embodiment, the processings in the step S4 and after in FIG. 3 are the same as those in the first embodiment. By performing such processings, similarly in the first embodiment in which determination result for the mucosal structure is acquired by using the structure of the running pattern of the blood vessels, it is possible to acquire the determination result for the epithelial structure as the mucosal structure using the running pattern of the epithelial tissue by replacing the blood vessels with the epithelial tissue.

Thus, in the present embodiment, similar circular-shaped structures included in the running pattern of the epithelial tissue in the case where the living mucosa has a normal living mucosal structure are detected from the endoscopic image acquired by picking up the image of the living mucosa as a diagnosis target, and it is detected whether or not the predetermined network shape is included based on the number of detected similar circular-shaped structures, the areas thereof, and the like.

Furthermore, in the present embodiment, depending on whether or not the detected predetermined network shape, that is, the region of the similar circular-shaped network shape is present at a rate equal to or larger than a threshold with respect to the region of the endoscopic image in which the similar circular-shaped network shape is detected, determination is made as to whether or not the epithelial structure is normal mucosal structure, and the determination result is notified to the surgeon. Then, the surgeon can efficiently perform diagnosis without missing the lesion part by referring to the determination result.

Therefore, according to the present embodiment, it is possible to provide a diagnosis supporting apparatus which is capable of supporting the surgeon to perform diagnosis, by detecting the predetermined network shape based on the number of similar circular-shaped structures, the areas thereof, and the like.

Note that the processing using the iris filter instead of the vector convergence index filter may be performed in the first embodiment, and the vector convergence index filter may be used instead of the iris filter in the second embodiment.

In addition, embodiments in which a part of the above-described embodiments are modified or deleted are also included in the present invention.

For example, in the processing in the step S7, instead of the squares, areas of other shapes such as an area of a circle may be used, for example. In addition, the processing in the step S9 may be omitted in FIG. 3. Furthermore, without performing the processing in the step S10, the processings from the steps S9 to S11 or the processings from the steps S8 to S11 may be performed.

Note that, in the above description, when the condition that the distances between the center points of the respective similar circular-shaped structures are equal to or smaller than the threshold Thre 3 is satisfied, the processing for connecting the similar circular-shaped structures which satisfy the condition is performed by respectively adding predetermined areas corresponding to the distances. In the above-described examples, when the distances are equal to or smaller than the threshold Thre 3, the larger the distances are, the larger the areas become. However, the present invention is not limited to such a case, and the areas may be determined according to the distances using reference information.

Specifically, an average value, or the average value and a variance of the distances between the respective similar circular-shaped structures in the case where the living mucosa is a reference living mucosa determined as a normal tissue are found out in advance, and the similar circular-shaped structures may be connected to each other by respectively adding areas such that when the distance between the structures is equal to the average value, the maximum area is made to correspond to the distance, and the larger the distance is deviated from the average value, the smaller area is made to correspond to the distance.

When such a configuration is specifically applied, the respective distances between the similar circular-shaped structures which satisfy a distance condition that the distance is equal to or smaller than the threshold, and areas corresponding to the respective distances (or the shapes having corresponding areas) are stored in advance in a lookup table as information storage means, for example. Then, the inter-structure connecting section 32a of the network detection section 32 reads out the information on the corresponding areas and the like from the lookup table with respect to the respective distances between the respective similar circular-shaped structures which satisfy the distance condition, and the appropriate similar circular-shaped structures may be connected to each other using the areas and the like. Note that it is preferable that information on the pixel size on the endoscopic image which corresponds to the average value can be referred to when using the lookup table.

In addition, similar circular-shaped structures are detected and the detected plurality of similar circular-shaped structures are connected to each other respectively with the areas corresponding to the distances between the respective structures, thereby allowing a predetermined network shape to be detected. However, the present invention is not limited to such a configuration, and the predetermined network shape may be detected based on the number of the similar circular-shaped structures, the areas of the similar circular-shaped structures, the distances between the respective similar circular-shaped structures, or the number of connections between the respective similar circular-shaped structures.

What is claimed is:
1. A diagnosis supporting apparatus comprising:
an image input section configured to input an endoscopic image acquired from a living mucosal tissue;

a structure detection section configured to detect a plurality of similar circular-shaped structures from an image signal corresponding to the endoscopic image inputted to the image input section;

a structure connecting section configured to connect the similar circular-shaped structures to each other by adding regions having diagonal lines that correspond to the distances between the center points, wherein the structure connecting section connects the plurality of similar circular-shaped structures detected by the structure detection section when distances between center points of the respective similar circular-shaped structures are equal to or smaller than a predetermined distance;

an overlapping integration section configured to integrate each of the regions overlapping each other into an aggregation;

a threshold processing section configured to determine among aggregations integrated by the overlapping integration section each of the aggregations that is equal to or larger than a predetermined threshold; and a network shape generation section configured to generate a predetermined network shape from each of the aggregations that the threshold processing section has determined is equal to or larger than the predetermined threshold.

2. The diagnosis supporting apparatus according to claim 1, further comprising a mucosal structure determination section which is configured to determine whether or not the endoscopic image has a predetermined mucosal structure as a diagnosis target, based on a determination result as to whether or not the region having the predetermined network shape generated by the network shape generation section is present in the endoscopic image at a rate equal to or larger than a second threshold.

3. The diagnosis supporting apparatus according to claim 2, further comprising a notification section configured to notify the determination result acquired by the mucosal structure determination section.

4. The diagnosis supporting apparatus according to claim 2, wherein the mucosal structure determination section determines whether or not a structure of a gastric fundic gland mucosa or a structure of a pit pattern of a colon is present as the predetermined mucosal structure which is the diagnosis target.

5. The diagnosis supporting apparatus according to claim 2, further comprising an information storage section configured to store, in advance, information including the distances between center points of the respective similar circular-shaped structures which are equal to or smaller than the predetermined distance and a shape corresponding to the distances between the center points, the distances and the shape corresponding to the distances between the center points being made to correspond to each other, wherein, when connecting the respective similar circular-shaped structures, the interstructure connection section connects between the respective similar circular-shaped structures by reading out the shape corresponding to the distances between the respective similar circular-shaped structures from the information storage section.

6. The diagnosis supporting apparatus according to claim 1, wherein the structure detection section detects a blood vessel candidate region in the living tissue by using a vector convergence index filter with respect to the image signal.

7. The diagnosis supporting apparatus according to claim 6, wherein the structure detection section detects a blood vessel candidate region in the living tissue by applying a similar circular-shaped filter with respect to the image signal or an image signal processed using the vector convergence index filter.

8. The diagnosis supporting apparatus according to claim 1, wherein the structure detection section detects an epithelial structure in the living tissue by using a point convergence index filter with respect to the image signal.

9. The diagnosis supporting apparatus according to claim 1, wherein the endoscopic image is an image picked up with reflection light of narrow-band light irradiated to the living tissue.

10. The diagnosis supporting apparatus according to claim 1, wherein the endoscopic image is an image in which a mucosal structure of the living tissue is enhanced by pigment dispersion or dyeing.

11. The diagnosis supporting apparatus according to claim 1, wherein the network shape generation section connects points to form the outer shape of the aggregation, wherein the threshold processing section has determined that the number of regions is equal to or larger than the predetermined threshold, and forms an outer shape of the aggregation in a convex shape outwardly as the predetermined network shape.

12. A method for processing an endoscopic image of a diagnosis supporting apparatus, the method comprising:

an image input step in which an image input section inputs an endoscopic image acquired from a living mucosal tissue;

a structure detection step in which a structure detection section detects a plurality of similar circular-shaped structures from an image signal corresponding to the endoscopic image inputted to the image input section;

a structure connecting step, wherein a structure connecting section connects the similar circular-shaped structures to each other by adding regions having diagonal lines that correspond to the distances between the center points, wherein the structure connecting section connects the plurality of similar circular-shaped structures detected by the structure detection section when distances between center points of the respective similar circular-shaped structures are equal to or smaller than a predetermined distance;

an overlapping integration step, wherein an overlapping integration section integrates each of the regions overlapping each other into an aggregation;

a threshold processing step, wherein a threshold processing section determines among aggregations integrated by the overlapping integration section each of the aggregations that is equal to or larger than a predetermined threshold;

a network shape generation step, wherein a network shape generating section generates a predetermined network shape from each of the aggregations that the threshold processing section has determined is equal to or larger than the predetermined threshold; and a display step, wherein a display displays the predetermined network shape from each of the aggregations.

* * * * *